United States Patent [19]

Krenzer

[11] 4,190,431
[45] Feb. 26, 1980

[54] SUBSTITUTED OXADIAZOLIDINE-3,5-DIONES

[75] Inventor: John Krenzer, Oak Park, Ill.

[73] Assignee: Velsicol Chemical Corporation, Chicago, Ill.

[21] Appl. No.: 703,497

[22] Filed: Nov. 17, 1967

Related U.S. Application Data

[62] Division of Ser. No. 535,323, Mar. 18, 1966, Pat. No. 3,437,664.

[51] Int. Cl.$^2$ ............................................. A01N 9/22
[52] U.S. Cl. .................................................. 71/92
[58] Field of Search ........................................ 71/92

[56] References Cited

U.S. PATENT DOCUMENTS

| | | | |
|---|---|---|---|
| 3,177,249 | 4/1965 | Martin et al. | 71/120 |
| 3,205,258 | 9/1965 | Simonian et al. | 71/120 |
| 3,254,984 | 6/1966 | Johnson | 71/120 |
| 3,257,190 | 6/1966 | Soper | 71/121 |
| 4,088,472 | 5/1978 | Stoffel et al. | 71/92 |

*Primary Examiner*—Glennon H. Hollrah
*Attorney, Agent, or Firm*—Robert J. Schwarz

[57] ABSTRACT

This invention is concerned with a method for destroying undesirable plant life which comprises applying to said plant life a herbicidally toxic amount of a herbicide containing a chemical compound of the formula

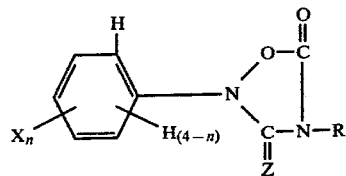

wherein R is selected from the group consisting of alkyl having 1 to 3 carbon atoms and alkenyl having 2 to 3 carbon atoms; Z is selected from the group consisting of oxygen and sulfur; X is selected from the group consisting of halogen, lower alkyl, lower alkenyl, lower haloalkyl, lower alkoxy, nitro, amino, lower alkylamino, lower dialkylamino, lower acylamino, N-lower alkyl-N-lower acylamino, lower alkylthio, lower alkylsulfoxide, lower alkyl sulfone, cyano, thiocyano and $$-N=CHR'$$

wherein R' is selected from the group consisting of hydrogen and lower alkyl; and n is an integer from 0 to 4, provided a maximum of two X's are selected from the group consisting of nitro, amino, lower alkylamino, lower dialkylamino, lower acylamino and N-lower alkyl-N-lower acylamino when n is greater than 2. The term "lower" as used herein means up to about ten carbon atoms.

1 Claim, No Drawings

SUBSTITUTED OXADIAZOLIDINE-3,5-DIONES

This application is a division of my co-pending application Ser. No. 535,323, filed Mar. 18, 1966, now U.S. Pat. No. 3,437,664.

This invention relates to new chemical compositions of matter. More particularly this invention relates to new chemical compositions of the formula

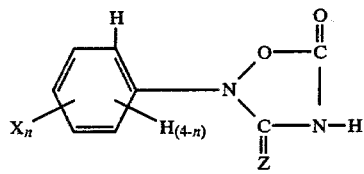

wherein R is selected from the group consisting of alkyl having 1 to 3 carbon atoms and alkenyl having 2 to 3 carbon atoms; Z is selected from the group consisting of oxygen and sulfur; X is selected from the group consisting of halogen, lower alkyl, lower alkenyl, lower haloalkyl, lower alkoxy, nitro, amino, lower alkylamino, lower dialkylamino, lower acylamino, N-lower alkyl-N-lower acylamino, lower alkylthio, lower alkylsulfoxide, lower alkyl sulfone, cyano, thiocyano and

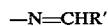

wherein R' is selected from the group consisting of hydrogen and lower alkyl; and n is an integer from 0 to 4, provided a maximum of two X's are selected from the group consisting of nitro, amino, lower alkylamino, lower dialkylamino, lower acylamino and N-lower alkyl-N-lower acylamino when n is greater than 2. The term "lower" as used herein means up to about ten carbon atoms.

In a preferred embodiment of this invention X is selected from the group consisting of halogen, lower alkyl, lower alkenyl, lower haloalkyl and nitro, and R, Z, and n are as heretofore described, provided that a maximum of two X's are nitro when n is greater than 2.

The compounds of the present invention are unexpectedly effective as pesticides and particularly as herbicides. Many of the compounds of the present invention are additionally effective as fungicides and as insecticides.

The new compounds of the present invention can be prepared readily by reacting a corresponding urea or thiourea of the formula

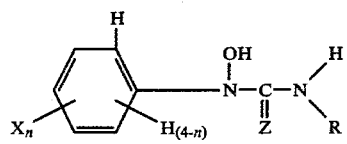

wherein R, Z, X and n are as heretofore described, with an alkyl chloroformate such as ethyl chloroformate. The reaction can be conveniently carried out in aqueous base such as aqueous sodium hydroxide solution by adding the alkyl chloroformate to the urea or thiourea at lower temperatures such as at 5°–20° C. The addition is preferably performed with stirring and the stirring continued after the addition. The desired compound can be recovered from the reaction mixture by methods common to the art such as filtration, decantation, extraction, washing, drying, recrystallizing, and the like.

The compounds of the present invention wherein at least one X is a primary or secondary amine can be prepared readily by hydrolysis of the corresponding acylamino compound. Compounds having at least one X selected from the group consisting of lower alkylsulfoxides and lower alkylsulfones can be prepared from the corresponding lower alkylthio compound by oxidation by methods known to the art.

Compounds wherein at least one X is an imine of the formula

can be prepared from the corresponding compound having an unsubstituted amino group in the position in which the imine group is desired by reacting with an appropriate aldehyde under dehydration conditions.

The starting material compounds of Formula II can be prepared readily from the corresponding N-arylhydroxylamine by reacting with an appropriate isocyanate or isothiocyanate of the formula

wherein R and Z are as heretofore described. This reaction can be carried out by adding the latter to a solution of the N-arylhydroxylamine in a suitable solvent such as diethyl ether. Low temperatures are preferred for this reaction such as from about 0° to 10° C. The starting material urea or thiourea can be used in the reaction solution as such, or can be recovered therefrom by precipitation upon adding a diluent such as pentane followed by filtration and drying.

Exemplary of suitable starting material urea and thiourea compounds are: 1-methyl-3-phenyl-3-hydroxyurea, 1-methyl-3-(3'-methylphenyl)-3-hydroxyurea, 1-methyl-3-(3',4'-dimethylphenyl)-3-hydroxyurea, 1-methyl-3-(3'-nitro-4'-methylphenyl)-3-hydroxyurea, 1-methyl-3-(3'-trifluoromethylphenyl)-3-hydroxyurea, 1-methyl-3-(4'-chlorophenyl)-3-hydroxyurea, 1-isopropyl-3-(4'-chlorophenyl)-3-hydroxyurea, 1-allyl-3-(2',3'-dichlorophenyl)-3-hydroxyurea, 1-methyl-3-(2',4',5'-trichlorophenyl)-3-hydroxyurea, 1-methyl-3-(3'-bromophenyl)-3-hydroxyurea, 1-methyl-3-phenyl-3-hydroxythiourea, 1-methyl-3-(4'-chlorophenyl)-3-hydroxythiourea, 1-methyl-3-(2',4',5'-trichlorophenyl)-3-hydroxythiourea, and the like.

The N-aryl hydroxylamines used in the above preparation of the starting material ureas and thioureas of the present invention can be prepared from the corresponding nitrobenzene.

Suitable isocyanates and isothiocyanates for use in preparing the starting material ureas and thioureas of the present invention are mono lower alkyl and lower alkenyl isocyanates and -isothiocyanates, such as, methyl isocyanate, ethyl isocyanate, n-propyl isocyanate, isopropyl isocyanate, allyl isocyanate, methyl isothiocyanate, ethyl isothiocyanate, allyl isothiocyanate, and the like.

The manner in which the new compounds of the present invention can be prepared readily is illustrated in the following examples:

EXAMPLE 1

Preparation of
2-Phenyl-4-methyl-1,2,4-oxadiazolidine-3,5-dione

1-Methyl-3-phenyl-3-hydroxyurea (10 g; 0.06 mole) was dissolved in a cooled (10° C.) 2 N aqueous sodium hydroxide (0.068 mole) solution (34 ml.). Ethyl chloroformate (6.3 ml; 0.066 mole) was added dropwise at 10°-15° C. with stirring. The stirring was continued for about ½ hour after the addition was completed. The desired compound, which precipitated as formed, was removed by filtration, washed with water and dried. The compound was recrystallized from methanol and dried under vacuum to yield solid 2-phenyl-4-methyl-1,2,4-oxadiazolidine-3,5-dione having a melting point of 98°-99° C. and the following elemental analysis as calculated for $C_9H_8N_2O_3$:

|  | C | H | N |
|---|---|---|---|
| Theoretical % | 56.28 | 4.19 | 14.58 |
| Found % | 56.62 | 4.64 | 14.50 |

EXAMPLE 2

Preparation of
2-(4'-chlorophenyl)-4-methyl-1,2,4-oxadiazolidine-3,5-dione

1-Methyl-3-(4'-chlorophenyl)-3-hydroxyurea (5.7 g.) was dissolved in benzene (30 ml.) to which triethylamine (3 drops) had been added. Methyl isocyanate (3.6 ml.) was added to the mixture. The reaction mixture was heated to and maintained at reflux for about 14 hours. Hexane (100 ml.) was added to the reaction mixture followed by powdered charcoal and the solution filtered and cooled. The desired compound precipitated from solution and was recrystallized from ethyl acetate in hexane mixture yielding white crystals of 2-(4'-chlorophenyl)-4-methyl-1,2,4-oxadiazolidine-3,5-dione melting 116°-118° C. and having the following elemental analysis as calculated for $C_9H_7ClN_2O_3$:

|  | C | H | Cl |
|---|---|---|---|
| Theoretical % | 47.65 | 3.11 | 15.64 |
| Found % | 47.80 | 3.49 | 15.60 |

EXAMPLE 3

Preparation of
2-(4'-chlorophenyl)-4-ethyl-1,2,4-oxadiazolidine-3,5-dione

A solution of ethyl isocyanate (7.6 g.) in diethyl ether (20 ml.) was added dropwise with stirring to a solution of N-(4-chlorophenyl) hydroxylamine in ether (60 ml.) at room temperature. Stirring was continued for one hour, during which time solid material precipitated from solution. Pentane (100 ml.) was added to the reaction mixture to precipitate additional 1-ethyl-3-(4'-chlorophenyl)-3-hydroxyurea. The desired compound was removed from the reaction mixture by filtration and was air dried.

1-Ethyl-3-(4'-chlorophenyl)-3-hydroxyurea (8.0 g; 0.037 mole) prepared above was dissolved in cooled (10° C.) 2 N aqueous sodium hydroxide (21 ml.). Ethyl chloroformate (3.9 ml; 0.041 mole) was added dropwise at 10°-15° C. with stirring and the stirring was continued for about ½ hour after addition was completed. The desired compound precipitated as formed and was removed by filtration, washed with water, air dried, and recrystallized from methanol to yield solid 2-(4'-chlorophenyl)-4-ethyl-1,2,4-oxadiazolidine-3,5-dione as tan needle-like crystals melting 84°-86° C. and having the following elemental analysis as calculated for $C_{10}H_9ClN_2O_3$:

|  | C | H | Cl |
|---|---|---|---|
| Theoretical % | 49.92 | 3.77 | 14.74 |
| Found % | 49.48 | 3.96 | 14.54 |

EXAMPLE 4

Preparation of
2-(4'-chlorophenyl)-4-allyl-1,2,4-oxadiazolidine-3,5-dione

Allyl isocyanate (5.8 g.) was added dropwise at 0° to 5° C. to a stirred solution of N-(4-chlorophenyl)-hydroxylamine (10 g.) dissolved in benzene (50 ml.). The reaction mixture was stirred for ½ hour at 15°-20° C., then cooled to 10° C. and the precipitated solid filtered. The solid was washed with hexane and dried to yield 1-allyl-3-(4'-chlorophenyl)-3-hydroxyurea as white crystals melting 117°-118° C.

1-Allyl-3-(4'-chlorophenyl)-3-hydroxyurea (6.0 g.) was dissolved in cooled dioxane (50 ml.) and a solution of sodium hydroxide (1.3 g.) in water (15 ml.) was added thereto. Ethyl chloroformate (3.2 g; 2.9 ml.) was added dropwise at 10°-15° C. with stirring and the stirring continued for about ½ hour after the addition was completed. The reaction mixture was poured into cold water (300 ml.), stirred and filtered to separate the precipitate. The precipitate was recrystallized from ethanol and dried in vacuo at room temperature to yield 2-(4'-chlorophenyl)-4-allyl-1,2,4-oxadiazolidine-3,5-dione as white needle-like crystals melting 56°-57° C. and having the following elemental analysis as calculated for $C_{11}H_9ClN_2O_3$:

|  | C | H | Cl |
|---|---|---|---|
| Theoretical % | 52.38 | 3.60 | 14.06 |
| Found % | 52.52 | 3.84 | 13.95 |

EXAMPLE 5

Preparation of
2-(2',4',5'-trichlorophenyl)-4-methyl-1,2,4-oxadiazolidine-3,5-dione 1-Methyl-3-(2',4',5'-trichlorophenyl)-3-hydroxyurea (8 g; 0.03 mole) was dissolved in cooled (10° C.) 2 N aqueous sodium hydroxide solution (18 ml.) and mixed with dioxane (80 ml.). Ethyl chloroformate (3.3 ml; 0.034 mole) was added dropwise to the reaction mixture at 10°-15° C. with stirring. The stirring was continued for about ½ hour after the addition was completed. The dark, oily product was separated and recrystallized from methanol and boiled with powdered charcoal to yield 2-(2',4',5'-trichlorophenyl)-4-methyl-1,2,4-oxadiazolidine-3,5-dione as tan needle-like crystals melting 112°-114° C. and having the following elemental analysis as calculated for $C_9H_5Cl_3N_2O_3$:

|  | C | H | Cl |
| --- | --- | --- | --- |
| Theoretical % | 36.58 | 1.70 | 36.02 |
| Found % | 36.88 | 1.68 | 35.70 |

EXAMPLE 6

Preparation of
2-(3'-Nitrophenyl)-4-methyl-1,2,4-oxadiazolidine-3,5-dione

A solution of N-(m-nitrophenyl) hydroxylamine (19.0 g.) in dioxane (100 ml.), water (25 ml.) and sodium bicarbonate (11.0 g.) was cooled to 5° C. Ethyl chloroformate (13.3 g; 11.8 ml.) was added to the solution and the mixture stirred at 5° C. for about ½ hour. The reaction mixture was poured into ice water (300 ml.) and the precipitate therefrom was removed by filtering and was dried by standing. The solid product was recrystallized from benzene-hexane mixture and dried under vacuum to yield ethyl (3-nitrophenyl)-N-hydroxyurethane as yellow crystals melting 103°–105° C.

Ethyl N-(3-nitrophenyl)-N-hydroxyurethane (6.0 g.) prepared above was added to benzene (30 ml.) and warmed to 50° C. to form a solution. Methyl isocyanate (3.3 g.) was added to the solution followed by triethylamine (3 drops). The reaction mixture was stirred for about 14 hours and then heated to distill off unreacted methyl isocyanate. The remaining mixture was heated under vacuum to remove the benzene and yield an oily solid which was recrystallized from ethyl acetate-hexane mixture and then from acetone-hexane mixture. The product thus obtained was 2-(3'-nitrophenyl)-4-methyl-1,2,4-oxadiazolidine-3,5-dione as white crystals melting 93°–94° C. and having the following elemental analysis as calculated for $C_9H_7N_3O_5$:

|  | C | H | N |
| --- | --- | --- | --- |
| Theoretical % | 45.61 | 2.98 | 17.72 |
| Found % | 45.97 | 3.43 | 17.55 |

EXAMPLE 7

Preparation of
2-(3'-Nitro-4'-methylphenyl)-4-methyl-1,2,4-oxadiazolidine-3,5-dione A solution of methyl isocyanate (4.1 g; 4.6 ml.) in diethyl ether (20 ml.) was added with stirring to a solution of N-(3-nitro-4-methylphenyl)-hydroxylamine (12.0 g.) in ether (70 ml.) at room temperature over a period of about 10 minutes. The yellow precipitate 1-methyl-3-(3'-nitro-4'-methylphenyl)-3-hydroxyurea which formed was filtered and air dried.

1-Methyl-3-(3'-nitro-4'-methylphenyl)-3-hydroxyurea (11 g; 0.049 mole) was dissolved in dioxane (80 ml.) and mixed with a 2 N aqueous sodium hydroxide (28.5 ml; 0.057 mole). Ethyl chloroformate (5.2 ml; 0.054 mole) was added dropwise at 10°–15° C. with stirring and the stirring continued for about ½ hour after the addition was completed. The product which precipitated as formed was removed by filtration, washed with water and dried. This product was recrystallized from methanol and dried under vacuum to yield 2-(3'-nitro-4'-methylphenyl)-4-methyl-1,2,4-oxadiazolidine-3,5-dione as yellow crystals melting 80°–81° C. and having the following elemental analysis as calculated for $C_{10}H_9N_3O_5$:

|  | C | H | N |
| --- | --- | --- | --- |
| Theoretical % | 47.84 | 3.61 | 16.74 |
| Found % | 48.02 | 4.02 | 16.16 |

EXAMPLE 8

Preparation of
2-(4'-fluorophenyl)-4-methyl-1,2,4-oxadiazolidine-3,5-dione p-Fluoronitrobenzene (14.1 g; 0.1 mole) was dissolved in tetrahydrofuran (100 ml.). Ten percent palladium on charcoal catalyst (0.1 g.) was added to the solution followed by hydrazine (6.0 ml; 0.105 mole), and the resulting mixture stirred at room temperature for about 48 hours with cooling as necessary. The reaction mixture containing N-(4-fluorophenyl) hydroxylamine was dried over anhydrous magnesium sulfate and filtered. To this solution was added methyl isocyanate (6.2 ml; 0.1 mole) and the mixture stirred for about 15 minutes. The reaction mixture was concentrated by distilling and then washed with hexane and filtered to yield 1-methyl-3-(4'-fluorophenyl)-3-hydroxyurea as a yellow solid.

1-Methyl-3-(4'-fluorophenyl)-3-hydroxyurea (10.0 g; 0.054 moles) was dissolved in dioxane (80 ml.) and mixed with a 2 N aqueous sodium hydroxide (32 ml; 0.064 mole). Ethyl chloroformate (5.7 ml; 0.06 mole) was added dropwise to the mixture at 10°–15° C. with stirring and the stirring continued for ½ hour after the addition was completed. The product which precipitated as formed was removed by filtration, washed with water and dried. The product was recrystallized from methanol and dried under vacuum to yield 2-(4'-fluorophenyl)-4-methyl-1,2,4-oxadiazolidine-3,5-dione as a solid melting 97°–99° C. and having the following elemental analysis as calculated for $C_9H_7FN_2O_3$:

|  | N |
| --- | --- |
| Theoretical % | 13.32 |
| Found % | 13.36 |

Other compounds within the scope of the present invention can be prepared readily by the procedures heretofore described. Presented in the following examples are the essential ingredients required to prepare the indicated named compounds according to the procedure detailed in the foregoing examples:

EXAMPLE 9

1-Methyl-3-(3',4'-dichlorophenyl)-3-hydroxyurea + sodium hydroxide + ethyl chloroformate = 2-(3',4'-dichlorophenyl)-4-methyl-1,2,4-oxadiazolidine-3,5-dione, m.p. 122°–123° C.

EXAMPLE 10

N-(p-Chlorophenyl)hydroxylamine ⇌ isopropyl isocyanate + sodium hydroxide + ethyl chloroformate = 2-(4'-chlorophenyl)-4-isopropyl-1,2,4-oxadiazolidine-3,5-dione, m.p. 61°–63° C.

EXAMPLE 11

N-(o-Chlorophenyl)hydroxylamine+methyl isocyanate+sodium hydroxide+ethyl chloroformate=2-(2'-chlorophenyl)-4-methyl-1,2,4-oxadiazolidine-3,5-dione m.p. 115°–116° C.

EXAMPLE 12

N-(2,5-Dichlorophenyl)hydroxylamine+isopropyl isocyanate+sodium hydroxide+ethyl chloroformate=2-(2',5'-dichlorophenyl)-4-isopropyl-1,2,4-oxadiazolidine-3,5-dione, m.p. 85°–88° C.

EXAMPLE 13

N-(2,3-Dichlorophenyl)hydroxylamine+allyl isocyanate+sodium hydroxide+ethyl chloroformate=2-(2',3'-dichlorophenyl)-4-allyl-1,2,4-oxadiazolidine-3,5-dione, m.p. 88°–89° C.

EXAMPLE 14

N-(3,4-Dimethylphenyl)hydroxylamine+ethyl chloroformate+sodium bicarbonate+methyl isocyanate=2-(3',4'-dimethylphenyl)-4-methyl-1,2,4-oxadiazolidine-3,5-dione, m.p. 93°–95° C.

EXAMPLE 15

N-(m-Trifluoromethylphenyl)hydroxylamine+methyl isocyanate+sodium hydroxide+ethyl chloroformate=2-(3'-trifluoromethylphenyl)-4-methyl-1,2,4-oxadiazolidine-3,5-dione, m.p. 51°–53° C.

EXAMPLE 16

N-(m-Chlorophenyl)hydroxylamine+methyl isocyanate+sodium hydroxide+ethyl chloroformate=2-(3'-chlorophenyl)-4-methyl-1,2,4-oxadiazolidine-3,5-dione, m.p. 75°–77° C.

EXAMPLE 17

N-(2-Methyl-3-chlorophenyl)hydroxylamine+methyl isocyanate+sodium hydroxide+ethyl chloroformate=2-(2'-methyl-3'-chlorophenyl)-4-methyl-1,2,4-oxadiazolidine-3,5-dione, m.p. 105°–107° C.

EXAMPLE 18

N-(m-Bromophenyl)hydroxylamine+methyl isocyanate+sodium hydroxide+ethyl chloroformate=2-(3'-bromophenyl)-4-methyl-1,2,4-oxadiazolidine-3,5-dione, m.p. 74°–75° C.

EXAMPLE 19

N-(2,4-Dichlorophenyl)hydroxylamine+methyl isocyanate+sodium hydroxide+ethyl chloroformate=2-(2',4'-dichlorophenyl)-4-methyl-1,2,4-oxadiazolidine-3,5-dione, m.p. 81°–83° C.

EXAMPLE 20

N-(m-Methylphenyl)hydroxylamine+methyl isocyanate+sodium hydroxide+ethyl chloroformate=2-(3'-methylphenyl)-4-methyl-1,2,4-oxadiazolidine-3,5-dione, m.p. 76°–77° C.

EXAMPLE 21

N-(3-Chloro-4-methylphenyl)hydroxylamine+ethyl chloroformate+sodium bicarbonate+methyl isocyanate=2-(3'-chloro-4'-methylphenyl)-4-methyl-1,2,4-oxadiazolidine-3,5-dione, m.p. 85°–88° C.

EXAMPLE 22 p-Nitrobenzonitrile+10% Pd on charcoal+hydrazine+methyl isocyanate+sodium hydroxide+ethyl chloroformate=2-(4'-cyanophenyl)-4-methyl-1,2,4-oxadiazolidine-3,5-dione.

EXAMPLE 23

N-(p-Methoxyphenyl)hydroxylamine+methyl isocyanate+sodium hydroxide+ethyl chloroformate=2-(4'-methoxyphenyl)-4-methyl-1,2,4-oxadiazolidine-3,5-dione.

EXAMPLE 24

N-(p-Methylthiophenyl)hydroxylamine+methyl isocyanate+sodium hydroxide+ethyl chloroformate=2-(4'-methylthiophenyl)-4-methyl-1,2,4-oxadiazolidine-3,5-dione.

EXAMPLE 25

N-[m-(Dimethylamino)phenyl]hydroxylamine+methyl isocyanate+sodium hydroxide+ethyl chloroformate=2-[( 3'-(dimethylamino)phenyl]-4-methyl-1,2,4-oxadiazolidine-3,5-dione.

EXAMPLE 26

N-(Phenyl)hydroxylamine+methyl isothiocyanate+sodium hydroxide+ethyl chloroformate=2-phenyl-4-methyl-3-thio-1,2,4-oxadiazolidine-3,5-dione.

EXAMPLE 27

N-(p-Chlorophenyl)hydroxylamine+methyl isothiocyanate+sodium hydroxide+ethyl chloroformate=2-(4'-chlorophenyl)-4-methyl-3-thio-1,2,4-oxadiazolidine-3,5-dione.

EXAMPLE 28

N-(2,4,5-Trichlorophenyl)hydroxylamine+methyl isothiocyanate+sodium hydroxide+ethyl chloroformate=2-(2',4',5'-trichlorophenyl)-4-methyl-3-thio-1,2,4-oxadiazolidine-3,5-dione.

For practical use as herbicides, the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in-oil) can be prepared for direct application to weed infestations.

A typical herbicidal composition according to this invention is illustrated by the following example, in which the quantities are in parts by weight.

EXAMPLE 29

| Preparation of a Dust | |
|---|---|
| Product of Example 3 | 10 |
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers; spreaders; deactivators; adhesives; stickers; fertilizers; activators; synergists, and the like.

The compounds of the present invention are also useful when combined with other herbicides and/or defoliants, dessicants, growth inhibitors, and the like, in the herbicidal compositions heretofore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), and the like; carbamate herbicides such as IPC, CIPC, swep, barban, and the like; thiocarbamate and dithiocarbamate herbicides such as CDEC, metham sodium, EPTC, diallate, PEBC, and the like; substituted urea herbicides such as dichloral urea, fenuron, monuron, diuron, linuron, monolinuron, neburon, and the like; symmetrical triazine herbicides such as simazine, chlorazine, atrazine, trietazine, simetone, prometone, propazine, ametryne, and the like; chloroacetamide herbicides such as α-chloro-N,N-dimethylacetamide, 2-chloro-N,N-diallylacetamide, CDEA, α-chloro-N-isopropyl acetamide, 4-(chloroacetyl)morpholine, 1-(chloroacetyl)piperidine, and the like; chlorinated aliphatic acid herbicides such as TCA, dalapon, 2,3-dichloropropionic acid, and the like, chlorinated benzoic acid and the phenylacetic acid herbicides such as 2,3,6-TBA, 2,3,5,6-TBA, dicamba, tricamba, amiben, fenac, 2-methoxy-3,6-dichlorophenylacetic acid, 3-methoxy-2,6-dichlorophenylacetic acid, 2-methoxy-3,5,6-trichlorophenylacetic acid, and the like; and such compounds as O,S-dimethyl tetrachlorothioterephthalate, methyl 2,3,5,6-tetrachloro-N-methoxy-N-methylterephthalamate, 2-[(4-chloro-o-tolyl)oxy]-N-methoxyacetamide, aminotriazole, phenyl mercuric acetate, endothal, biuret, technical chlordane, dimethyl 2,3,5,6-tetrachloroterephthalate, diquat, erbon, DNC, DNBP, dichlobenil; DPA, diphenamid, dipropalin, trifluralin, solan, dicryl, merphos, DMPA and the like. Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed lambsquarters, foxtail, crabgrass, wild mustard, field pennycress, ryegrass, goose-grass, chickweed, wild oats, velvet leaf, purselane, barnyard grass, and smartweed; biennials such as wild carrot, great burdock, mullein, round-leaved mallow, blue thistle, bull thistle, hounds-tongue, moth mullein, and purple star thistle; or perennials such as white cockle, perennial rye-grass, quackgrass, Johnson grass, Canada thistle, hedge bindweed, Bermuda grass, sheep sorrel, curly dock, nutgrass, field chickweed, and winter-cress. Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. Thus, the new compounds at the rates required do not significantly injure rice and their use results in increased rice yields. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the applications of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of crabgrass. In these experiments small plastic greenhouse pots filled with dry soil were seeded with crabgrass. Twenty-four hours or less after seeding the pots were sprayed with water until the soil was wet and the test compounds formulated as aqueous emulsions of acetone solutions containing emulsifiers were sprayed at the indicated concentrations on the surface of the soil. After spraying, the soil containers were placed in the greenhouse and provided with supplementary heat as required and daily or more frequent watering. The plants were maintained under these conditions for a period of from 15 to 21 days at which time the condition of the plants and the degree of injury to the plants were rated on a scale of from 0 to 10, as follows: 0=no injury, 1,2=slight injury, 3,4=moderate injury, 5,6=moderately severe injury, 7,8,9=severe injury and 10=death. The effectiveness of these compounds is demonstrated by the following data:

| Compound of | Dosage Concn. Actual Chemical Compound per Acre | Injury Rating |
| --- | --- | --- |
| Example 8 | 4 | 9.5 |
| Example 9 | 4 | 10 |
| Example 16 | 4 | 10 |
| Example 20 | 4 | 7 |

The above experiments were repeated except that the pots were seeded with dock rather than crabgrass. The effectiveness of these compounds is demonstrated by the following data:

| Compound of | Dosage Concn. Actual Chemical Compound Per Acre | Injury Rating |
| --- | --- | --- |
| Example 2 | 2 | 8 |
| Example 2 | 4 | * |
| Example 5 | 2 | 10 |
| Example 5 | 4 | * |
| Example 7 | 4 | 10 |
| Example 9 | 4 | 10 |
| Example 16 | 4 | 10 |
| Example 20 | 4 | 10 |

* — Not tested

The herbicidal activity of the compounds of this invention was also demonstrated by experiments carried out for the post emergence control of pigweed. In these experiments the compounds to be tested were formulated as aqueous emulsions and sprayed at the indicated dosage on the foliage of pigweed plants that had attained a prescribed size. After spraying the plants were placed in a greenhouse and watered daily or more frequently. Water was not applied to the foliage of the treated plants. The severity of the injury was determined 10 to 15 days after treatment and was rated on the scale of from 0 to 10 heretofore described. The effectiveness of these compounds is demonstrated by the following data:

| Compound of | Dosage Concn. Actual Chemical Compound Per Acre | Injury Rating |
| --- | --- | --- |
| Example 2 | ½ | 10 |
| Example 5 | ½ | 8 |
| Example 9 | ½ | 10 |

The above experiments were repeated except that kochia plants were used in place of pigweed plants. The effectiveness of these compounds is demonstrated by the following data:

| Compound of | Dosage Concn. Actual Chemical Compound Per Acre | Injury Rating |
| --- | --- | --- |
| Example 7 | 1 | 10 |
| Example 16 | 1 | 10 |
| Example 20 | 1 | 10 |

The above experiments were repeated except that barnyard grass plants were used in place of kochia plants. The effectiveness of these compounds is demonstrated by the following data:

| Compound of | Dosage Concn. Actual Chem. Compound Per Acre | Injury Rating |
| --- | --- | --- |
| Example 2 | ½ | 10 |
| Example 2 | 1 | * |
| Example 5 | ½ | 3 |
| Example 5 | 1 | 10 |
| Example 9 | ½ | 10 |
| Example 9 | 1 | 10 |

* — Not tested.

I claim:

1. A method of destroying undesired vegetation which comprises applying to said vegetation a herbicidally effective amount of the compound 2-(3',4'-dichlorophenyl)-4-methyl-1,2,4-oxadiazolidine-3,5-dione.

* * * * *